United States Patent [19]

Lang

[11] Patent Number: 4,734,516
[45] Date of Patent: Mar. 29, 1988

[54] PROCESS FOR THE PREPARATION OF PARTIALLY HALOGENATED 1-PROPANOLS

[75] Inventor: Robert W. Lang, Pratteln, Switzerland

[73] Assignee: Ciba-Geigy Corporation, Ardsley, N.Y.

[21] Appl. No.: 841,399

[22] Filed: Mar. 19, 1986

[30] Foreign Application Priority Data

Mar. 28, 1985 [CH] Switzerland ............... 1346/85

[51] Int. Cl.$^4$ .................. C07C 31/34; C07C 29/64; C07C 33/46; C07C 67/343; C07C 29/46; C07C 69/96

[52] U.S. Cl. .................. 558/54; 558/60; 558/204; 558/385; 558/425; 558/436; 558/440; 558/461; 260/502.4 R; 260/502.6; 260/503; 260/513 R; 260/513 T; 560/330; 560/336; 560/356; 562/512; 562/579; 562/586; 564/201; 564/209; 564/305; 564/442; 564/443; 568/55; 568/812; 568/842; 568/878; 568/924

[58] Field of Search ........... 568/842, 878, 812, 55, 568/649, 924; 260/239, 513, 502.6, 513 T, 502.4 R, 503, 513 R; 549/206; 562/586, 579, 512; 564/209, 463, 503, 510, 201, 305, 442, 443, 371; 558/385, 425, 436, 440, 461, 54, 60, 204; 560/356, 330, 336

[56] References Cited

U.S. PATENT DOCUMENTS

| | | | |
|---|---|---|---|
| 2,568,500 | 9/1951 | Husted et al. | 260/601 |
| 2,824,897 | 2/1958 | Wujciak et al. | 260/633 |
| 3,290,333 | 12/1966 | Fainberg et al. | 549/206 |
| 3,732,274 | 5/1973 | Young et al. | 260/463 |

FOREIGN PATENT DOCUMENTS

| | | |
|---|---|---|
| 73569 | 3/1983 | European Pat. Off. |
| 157739 | 10/1985 | European Pat. Off. |
| 0187674 | 7/1986 | European Pat. Off. |
| 1816282 | 12/1968 | Fed. Rep. of Germany |
| 2557162 | 7/1976 | Fed. Rep. of Germany |
| 1496633 | 9/1967 | France |
| 1122847 | 8/1968 | United Kingdom |
| 1474867 | 5/1977 | United Kingdom |

OTHER PUBLICATIONS

J. Fluorine Chem. 22:585, (1983).
J.C.S. Chem. Comm., pp. 885–886, (1976).
Collection Czechoslov. Chem. Commun. 37:3946–3949, (1972).
Hemer et al., *J. Fluorine Chem.*, 29, 86, (1985), pp. 86.
Monison, Organic Chemistry, 3rd ed, 1973, pp. 512–513.
Journal of Fluorine Chem., vol. 29, (1985).

*Primary Examiner*—Richard L. Raymond
*Assistant Examiner*—Raymond Covington
*Attorney, Agent, or Firm*—Michael W. Glynn; Irving M. Fishman

[57] ABSTRACT

The reaction of a zinc compound compound of formula III $$CF_3CCl_2ZnCl.yL \qquad (III)$$

wherein y is 1 or 2 and L is a solvent ligand selected from the group consisting of the N-disubstituted acid amides, N-substituted lactams and organic sulfoxides, with an aldehyde of formula II $$R-CHO \qquad (II)$$

wherein R is an aliphatic or aromatic hydrocarbon radical or an aliphatic or aromatic heterocyclic radical, gives 1-propanols of formula I $$CF_3CCl_2-\underset{\underset{\displaystyle |}{R}}{C}H-OH, \qquad (I)$$

in high yields.

16 Claims, No Drawings

PROCESS FOR THE PREPARATION OF PARTIALLY HALOGENATED 1-PROPANOLS

The present invention relates to a process for the preparation of trifluorodichloropropanols by reacting an organic zinc compound with an aldehyde.

The preparation of 3,3,3-trifluoro-2,2-dichloro-1-propanol by reacting formaldehyde, hydrofluoric acid and 1,1-dichloro-2,2-difluoroethylene in an autoclave at elevated temperature is described in French patent specification 1 496 633. The compound is obtained in only very low yield (less than 2%). 1,1-Dichloro-2,2-difluoroethylene is expensive and, in addition, must be processed in an autoclave owing to its volatility. Such a procedure is uneconomic.

The present invention relates to a process for the preparation of partially halogenated 1-propanols of formula I $$CF_3CCl_2-\overset{R}{\underset{|}{C}H}-OH, \qquad (I)$$

wherein R is a hydrogen atom or an unsubstituted or substituted aliphatic or aromatic hydrocarbon radical or an unsubstituted or substituted aliphatic or aromatic heterocyclic radical which is linked through a carbon atom to the CH group in formula I, by reacting a zinc compound with an aldehyde, which process comprises reacting an aldehyde of formula II $$R-CHO \qquad (II)$$

wherein R is as defined above, in an inert solvent, with a zinc compound of formula III $$CF_3CCl_2ZnCl.yL \qquad (III)$$

wherein y is 1 or 2 and L is a solvent ligand selected from the group of the N-disubstituted acid amides, N-substituted lactams and organic sulfoxides, excepting the reaction of $CF_3CCl_3$ with an aldehyde RCHO in the presence of zinc, and subsequently isolating the 1-propanol of formula I.

R as a hydrocarbon radical in formula I preferably contains 1 to 30, in particular 1 to 20 and, most preferably, 1 to 12, carbon atoms. R as a heterocyclic radical preferably contains 1 to 3 heteroatoms in the ring. The ring preferably contains 4 to 8, most preferably 5 or 6, ring members. The hetero atoms are preferably O, S or N and may be the same or different. The radical R is unsubstituted or substituted by preferably 1 to 3 substituents.

R as an aliphatic hydrocarbon radical is preferably unsubstituted or substituted alkyl, alkenyl, alkynyl, cycloalkyl or cycloalkenyl. As an unsubstituted or substituted aromatic hydrocarbon radical, R is aryl, aralkenyl, aralkynyl or aralkyl. As an unsubstituted or substituted heterocyclic aliphatic radical, R is a 4- to 6-membered heterocyclic ring which contains 1 or 2 hetero atoms; and as an aromatic heterocyclic radical, R is a 5- or 6-membered heterocyclic ring which contains 1 or 2 hetero atoms. Alkyl, alkenyl and alkynyl may be linear or branched. Alkyl may be methyl, ethyl, n-propyl, isopropyl, n-butyl, isobutyl and tert-butyl, pentyl, hexyl, octyl, 2-ethylhexyl, nonyl, decyl, undecyl, dodecyl, tetradecyl, octadecyl and eicosyl.

Alkenyl is for example vinyl, allyl, 1- or 2-methylvinyl, styryl, butenyl, pentenyl, hexenyl, octenyl, decenyl and dodecenyl. Alkynyl may be ethynyl, propargyl, methylethynyl, phenylethynyl, butynyl, pentynyl, hexynyl, octynyl, decynyl and dodecynyl.

Cycloalkyl and cycloalkenyl may contain 3 to 12, preferably 3 to 8 and, most preferably, 3 to 6 ring carbon atoms. Typical examples are: cyclopropyl, cyclobutyl, cyclopentyl, cyclohexyl, cycloheptyl, cyclooctyl, cyclononyl, cyclodecyl, cyclododecyl, cyclopropenyl, cyclobutenyl, cyclopentadienyl, cyclohexenyl, cyclohexadienyl, cyclooctenyl, cyclooctadienyl, bicyclo-2,2,2-octenyl, bicyclo-2,2,1-heptenyl.

The aromatic hydrocarbon radical may be mononuclear or polynuclear and fused. Preferred aromatic hydrocarbon radicals are aryl, aralkenyl, aralkynyl or aralkyl of preferably 6 to 18, 7 to 18 and 8 to 18 carbon atoms respectively. Aryl is preferably phenyl or naphthyl. Examples of such radicals are: phenyl, naphthyl, benzyl, phenylethyl, 2-phenylpropyl, naphthylmethyl, dihydronaphthalene, indane, indene, fluorenone and phenanthrene.

R as an aliphatic heterocyclic radical may contain 3 to 7, preferably 4 to 6, ring members and, depending on the size of the ring, preferably 1 or 2 hetero atoms such as O, S or N. Examples of heterocyclic rings from which the radical R is derived are: oxetan, oxolan, oxolene, oxane, dioxane, aziridine, azetidine, azetine, pyrrolidine, pyrroline, tetrahydrothiophene, 2,3-dihydroindole, dihydrocumarone, dihydrothionaphthene, pyrazolidine, imidazolidine, oxazolidine, thiazolidine, triazolidine, oxadiazolidine, morpholine, piperidine, tetrahydroquinoline.

R as an aromatic heterocyclic radical preferably contains 1 to 3, most preferably 1 or 2, hetero atoms such as O, S and N and is preferably a 5- or 6-membered ring. Fused ring systems are also possible. Examples of aromatic heterocyclic rings from which R may be derived are: pyrrole, furan, thiophene, pyridine, pyran, pyrazole, imidazole, benzimidazole, triazine, oxazole, thiazole, pyrimidine, pyrazine, quinoline, chromene, purine and xanthene.

The radical R may be substituted by one or more, preferably by three, identical or different radicals. Examples of suitable substituents of R are: $C_1$–$C_{18}$alkyl, $C_2$–$C_{18}$alkenyl, $C_2$–$C_{18}$alkinyl, $C_6$–$C_{18}$aryl, $C_7$–$C_{18}$aralkyl, $C_7$–$C_{18}$alkaryl, $C_8$–$C_{18}$alkarylalkyl, $C_1$–$C_{18}$alkoxy, $C_1$–$C_{18}$alkylthio, $C_6$–$C_{18}$aryloxy, $C_7$–$C_{18}$aralkoxy, $C_7$–$C_{18}$aralkylthio, $C_7$–$C_{18}$alkaryloxy, $C_8$–$C_{18}$alkaralkoxy, $C_7$–$C_{18}$aryloxyalkyl, $C_7$–$C_{18}$alkoxyaryl, $C_3$–$C_{12}$cycloalkyl, $C_3$–$C_{12}$cycloalkoxy, $C_3$–$C_{12}$cycloalkenyl, $C_3$–$C_{12}$cycloalkenyloxy, —COOH, —CONH$_2$, —COOR$^1$, —CONHR$^1$, —CONR$^1$R$^2$, wherein R$^1$ is $C_1$–$C_{18}$alkyl, cyclohexyl, phenyl or benzyl and R$^2$ independently has the same meaning as R$^1$; —CN, —OH, —SH, —SO$_2$H, —SO$_3$H, —SO$_2$R$^1$, —SO$_3$R$^1$, —PO$_2$H, —PO$_3$H$_2$, —PO$_2$R$^1$, —PO$_3$R$^1$, —NO$_2$, —NH$_2$, —NHR$^1$, —NR$^1$R$^2$, F, Cl, Br, I and —NCO. The aliphatic radicals R may be interrupted by —CO— or —C(O)O—.

Aryl is preferably phenyl. Preferred substituents are: $C_1$–$C_{12}$alkyl, phenyl, benzyl, $C_7$–$C_{14}$alkylphenyl, $C_8$–$C_{14}$alkylbenzyl, $C_1$–$C_{12}$alkoxy, phenoxy, benzyloxy, $C_7$–$C_{12}$alkylphenoxy, $C_8$–$C_{14}$alkylbenzyloxy, $C_7$–$C_{12}$phenoxyalkyl, $C_7$–$C_{14}$alkoxyphenyl, cyclopentyl, cyclohexyl, —COOH, —CONH$_2$, —COOR$^1$ where R$^1$ is $C_1$–$C_{12}$-alkyl; CN, OH, SH, NH$_2$, NO$_2$, F, Cl, Br, and the aliphatic radicals may be interrupted as defined hereinabove.

Typical examples of such substituents are: methyl, ethyl, propyl, butyl, vinyl, allyl, ethynyl, propargyl, phenyl, benzyl, methylbenzyl, methylphenyl, methoxy, ethoxy, propoxy, butoxy, methylthio, phenoxy, benzyloxy, methylphenoxy, methylbenzyloxy, phenoxymethyl, methoxyphenyl, cyclopentyl, cyclohexyl, cyclohexenyl, cyclohexyloxy, methoxycarbonyl, methylamino, dimethylamino, methylaminocarbonyl, alkoxyalkyl such as methoxymethyl or methoxyethyl, alkylaminoalkyl such as methylaminomethyl or dimethylaminoethyl, phenoxyphenyl, methoxycarbonylmethyl or ethoxycarbonylethyl.

These substituents may in turn be substituted. Examples of such substituents are: chlorophenoxy, fluorobenzyloxy, hydroxyalkyl such as hydroxyethyl, haloalkyl such as chloromethyl, dichloromethyl, trichloromethyl, trifluoromethyl, carboxyphenyl, methoxycarbonylphenyl, and cyanoalkyl such as cyanoethyl.

In a preferred subgroup, R is $C_1$–$C_4$alkyl, $C_5$cycloalkyl or $C_6$cycloalkyl, $C_1$–$C_4$haloalkyl or unsubstituted or substituted phenyl or benzyl. Preferred substituents are Cl, $C_1$–$C_4$alkyl, $C_1$–$C_4$alkoxy, $C_1$–$C_4$alkylthio, phenylthio and benzylthio.

The reaction is preferably carried out in the temperature range from 0° to 80° C., in particular from 0° to 50° C. and, most preferably at room temperature, and the reaction time may be from several hours to several days. If the reaction is carried out by applying ultrasonic irradiation, e.g. in the range from 22–38 kHz, then it is possible to shorten the reaction time considerably. It is expedient to carry out the reaction in an inert gas atomsphere, e.g. nitrogen or a rare gas, and with the exclusion of air and moisture.

The aldehydes of formula II are known, commercially available, or they can be prepared by known methods. It is advantageous to use the reactants in equimolar amounts, but it may sometimes be expedient to use a small excess of the aldehydes of formula II.

The zinc compounds of formula III are novel. In formula III, L as an N-disubstituted acid amide is preferably a carboxamide, in particular one of the formula

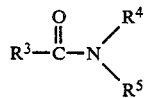

wherein $R^3$ is a hydrogen atom, alkyl of 1 to 12, preferably 1 to 4, carbon atoms, which is unsubstituted or substituted by halogen, preferably by fluorine or chlorine, or is cycloalkyl containing 4 to 7 ring carbon atoms which is unsubstituted or substituted by $C_1$–$C_4$alkyl or halogen, or is alkenyl of 2 to 12, preferably 2 to 4, carbon atoms, phenyl, benzyl or —$NR^4R^5$, where $R^4$ and $R^5$ are each independently of the other $C_1$–$C_{12}$alkyl, cycloalkyl containing 5 or 6 ring carbon atoms, or $R^4$ and $R^5$, when taken together, are tetramethylene or pentamethylene, each of which may be interrupted by —O—, —S— or —$NR^6$ ($R^6$=$C_1$–$C_4$alkyl).

$R^3$ is preferably a hydrogen atom or methyl. $R^4$ and $R^5$ are preferably methyl or ethyl.

Examples of acid amides are dimethylformamide, diethylformamide, dimethylacetamide, tetramethylurea and N-formylpyrrolidine. Dimethylformamide is particularly preferred.

L as N-substituted lactam preferably has the formula

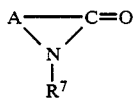

wherein A is dimethylene, trimethylene, tetramethylene or pentamethylene, and $R^7$ is $C_1$–$C_{12}$alkyl, preferably $C_1$–$C_4$alkyl, cyclohexyl or cyclopentyl. $R^7$ is preferably methyl or ethyl. Examples of such lactams are N-methylpropiolactam, N-methylpyrrolidone, N-ethylpyrrolidone, N-methylpiperidinone, N-methyl-ϵ-caprolactam, with N-methylpyrrolidone being preferred.

L as an organic sulfoxide corresponds preferably to the formula

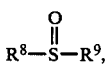

wherein each of $R^8$ and $R^9$ independently of the other is $C_1$–$C_{12}$alkyl, preferably $C_1$–$C_4$alkyl, or $R^8$ and $R^9$, when taken together, are tetramethylene or pentamethylene. Examples of organic sulfoxides are: dimethyl sulfoxide, methylethyl sulfoxide, diethyl sulfoxide, tetramethylene sulfoxide and pentamethylene sulfoxide.

Preferred zinc compounds of formula III are those in which L is an N-disubstituted carboxamide. In formula III, y is preferably 2. A particularly preferred zinc compound is $CF_3CCl_2ZnCl.2$ dimethylformamide.

The zinc compounds of formula III are prepared in a manner known per se by the direct reaction of zinc, preferably in the form of zinc dust, with 1,1,1-trifluoro-2,2,2-trichloroethane, excluding air and moisture and in an inert organic solvent in the presence of the solvent ligand. Preferably, the solvent corresponds to the solvent ligand. It is advantageous to cool the reaction mixture. The zinc compounds of this invention can then be isolated in conventional manner by removing the solvent or by crystallisation.

Another preparatory method comprises dissolving the known ether adducts of $CF_3CCl_2ZnCl$ (q.v. U.S. Pat. No. 3,290,333) in a solvent L and heating the solution to about 100° C., whereupon the adducts of the invention are formed by ligand exchange and can then be isolated in known manner.

The zinc compounds of formula III are crystalline compounds which are stable when air and moisture are excluded.

Suitable inert organic solvents are preferably polar solvents, most preferably polar aprotic solvents, which are used alone or in mixtures of at least two solvents. Examples of suitable solvents are: ethers such as diethyl ether, dibutyl ether, tetrahydrofuran, dioxane, dimethyl ethylene glycol ether, dimethyl diethylene glycol ether, diethyl diethylene glycol ether, dibutyl diethylene glycol ether, dimethyl triethylene glycol ether, carboxylates and lactones such as propylene carbonate, ethyl acetate, methyl propionate, ethyl benzoate, ethyl glycol diacetate, 2-methoxyethyl acetate, γ-butyrolactone, γ-valerolactone and mevalolactone; sulfoxides such as dimethyl sulfoxide, tetramethylene sulfoxide; sulfones such as dimethyl sulfone, diethyl sulfone, trimethylene sulfone, tetramethylene sulfone; and in particular N-disubstituted acid amides such as dimethylformamide, dimethylacetamide, N-methylpyrrolidone and hexamethylphosphoric triamide. Dimethylformamide is particularly preferred.

In a preferred embodiment of the process of this invention, the inert solvent corresponds to the solvent ligand L.

It has proved expedient to prepare the zinc compound of formula III in situ in a first reaction step, e.g. by reacting metallic zinc with $CF_3$—$CCl_3$ in a solvent corresponding to the solvent ligand L. However, it is also possible to dissolve a zinc compound of formula III first in an inert solvent.

To isolate the compounds of formula I, the reaction mixture can first be treated with an acid, preferably a dilute aqueous acid such as hydrochloric acid or sulfuric acid. This is done by pouring the reaction mixture into the dilute acid, which may be mixed with ice. Then a solvent, e.g. an ether, is added and the aqueous phase is mixed with the organic phase to extract the compounds. After separating the organic phase, the crude compound may be obtained by evaporating off the solvent. The crude product can be purified in conventional manner by crystallisation, distillation or chromatography.

The process of this invention affords the compounds of formula I in high yield and purity under mild reaction conditions and in simple technical apparatus. It is especially advantageous that no metallic zinc is present in the reaction mixture simultaneously with an aldehyde, whereby secondary reactions, e.g. the reduction of substituents in the aldehyde, are avoided.

The compounds of formula I are valuable intermediates for synthesising compounds containing $CF_3$ groups in the pharmaceutical and agrochemical fields. It has also been found that the alcohols of formula I, and especially their chloroformates, are admirably suited for use as O- or N-protective groups, particularly in peptide synthesis (q.v. European published patent application EP-A-O 157 739). These protective groups can be removed under mild reaction conditions. In addition, they have enhanced lipophilic properties which can also be varied within a wide range by choice of the radical R. These enhanced lipophilic properties also make possible reactions in less polar solvents and, in addition, the protective group can be specifically adapted to the respective reaction conditions.

The following Examples illustrate the invention in more detail.

EXAMPLES 1-3

65.4 g (1 mole) of zinc dust (activated according to Fieser & Fieser) are suspended in 500 ml of dimethylformamide in a three-necked flask and then 188 g (120 ml; 1 mole) of $CF_3CCl_3$ which has been freshly dried over a molecular sieve and subsequently distilled are added slowly to this suspension. After a few minutes the zinc begins to dissolve and the reaction mixture exotherms. The reaction temperature is kept below 30° C. by external cooling. The batch is then stirred for 1 hour and filtered over "Selecta" filter flakes (available from Schleicher & Schüll). With efficient stirring, 1 mole of aldehyde (see following Table) is added to the clear, reddish brown filtrate and the batch is stirred until the reaction is complete. Then the solution is poured into a mixture of 500 ml of 10% aqueous HCl and 300 g of ice and extracted with 5×300 ml of ethyl ether. The combined extracts are washed with 200 ml of 2% aqueous HCl, dried over $MgSO_4$ and concentrated by rotary evaporation. The residue is distilled in Example 1, recrystallised in Example 3, and chromatographed in Example 2. The yields are: 70% in Example 1, 82% in Example 2 and 91% in Example 3.

(b) In a 1 liter three-necked flask, 500 ml of dimethylformamide are added to 1 mole of $CF_3CCl_2ZnCl$·diethyl ether in an inert gas atmosphere with external cooling. After the mixture has reached room temperature, 1 mole of aldehyde is added with efficient stirring (see following Table) and the mixture is stirred until the reaction is complete. Working up is effected as described in (a). The yields are: 70% in Example 1, 78% in Example 2 and 89% Example 3.

| Example | R | $\delta H\alpha^{(a)}$ | m.p./b.p. (°C.) |
|---|---|---|---|
| 1 | $CCl_3$ | 4.80 ppm | 85°/26 mbar |
| 2 | $o\text{-}C_6H_5CH_2SC_6H_4$ | 5.82 ppm | yellow oil |
| 3 | 2,6-dimethoxyphenyl | 5.92 ppm | 75° (colourless crystals) |

$^{(a)1}$H—NMR ($CDCl_3$) δ rel. to TMS = 0 ppm

What is claimed is:

1. A process for the preparation of a partially halogenated 1-propanol of the formula

comprising
reacting an aldehyde of the formula

R—CHO   (II)

in an inert solvent with a zinc compound of the formula

with the exception of the reaction of $CF_3CCl_3$ and an aldehyde of formula II in the presence of zinc, and isolating the resultant 1-propanol of formula I; wherein y is one or two;

L is a solvent ligand selected from an N-disubstituted acid amide, an N-substituted lactam, and an organic sulfoxide; and R is a hydrogen atom; an unsubstituted or substituted, aliphatic or aromatic, hydrocarbon radical of 1–30 carbon atoms; each of said aliphatic radicals being uninterrupted or interrupted by —C(O)— or —C(O)O—; said substituents of the R radical being selected from $C_{1-18}$alkyl, $C_{2-18}$alkenyl, $C_{2-18}$alkynyl, $C_{6-18}$aryl, $C_{7-18}$aralkyl, $C_{7-18}$alkaryl, $C_{8-18}$alkarylalkyl, $C_{1-8}$alkoxy, $C_{1-8}$alkylthio, $C_{6-18}$aryloxy, $C_{7-18}$aralkoxy, $C_{7-18}$aralkylthio, $C_{6-8}$aryloxy, $C_{7-18}$aralkoxy, $C_{7-18}$aralkylthio, $C_{7-18}$alkaryloxy, $C_{8-18}$alkarylalkoxy, $C_{7-18}$aryloxyarlkyl, $C_{7-18}$alkoxyaryl, $C_{3-12}$cycloalkyl, $C_{3-12}$cycloalkoxy, $C_{3-12}$cycloalkenyl, $C_{3-12}$cycloalkenyloxy, —COOH, —CONH$_2$, —COOR$^1$, —CONHR$^1$, —CONR$^1$R$^2$, —CN, —OH, —SH, —SO$_2$H, —SO$_3$H, —SO$_2$R$^1$, —SO$_3$R$^1$, —PO$_2$H, —PO$_3$H$_2$, —PO$_2$R$^1$, —PO$_3$R$^1$, —NO$_2$, —NH$_2$, —NHR$^1$, —$NR^1R^2$, F, Cl, Br, I, and —NCO; $R^1$ and $R^2$ independently being selected from $C_{1-18}$alkyl, cyclohexyl, phenyl, or benzyl;

said substituents on R being unsubstituted or further substituted by halogen, hydroxy, carboxy, cyano, or methoxy carbonyl.

2. A process according to claim 1, wherein the reaction is carried out at room temperature.

3. A process according to claim 1, wherein the reaction is carried out by applying ultrasonic irradiation.

4. A process according to claim 1, wherein the solvent is a polar aprotic solvent.

5. A process according to claim 1, wherein the solvent is an N-disubstituted acid amide.

6. A process according to claim 1, wherein the 1-propanol of formula I is isolated by treating the reaction mixture with a dilute aqueous acid.

7. A process according to claim 1, wherein the inert solvent corresponds to the solvent ligand L in formula III.

8. A process according to claim 1, wherein equimolar amounts of the aldehyde of formula II and the zinc compound of formula III are used.

9. A process according to claim 1, wherein the zinc compound of formula III is prepared in a first step in situ and then reacted with an aldehyde of formula II.

10. A process according to claim 1, wherein a zinc compound of formula III is dissolved in an inert solvent and then reacted with an aldehyde of formula II.

11. A process according to claim 1, wherein the reaction is carried out in an inert gas.

12. A process according to claim 1, wherein L in formula III is an N-disubstituted carboxamide.

13. A process according to claim 1, wherein y in formula III is 2.

14. A process according to claim 1, wherein the zinc compound of formula III is $CF_3CCl_2ZnCl.2$ dimethylformamide.

15. A process according to claim 1, wherein R in formula II carries one to three substituents.

16. A process according to claim 1, wherein R in formula II as an aliphatic hydrocarbon radical is unsubstituted or substituted alkyl, alkenyl, alkynyl, cycloalkyl or cycloalkenyl; and as an unsubstituted or substituted aromatic hydrocarbon radical is aryl, aralkenyl, aralkynyl or aralkyl.

* * * * *